US012751831B2

(12) United States Patent
Dye, Jr. et al.

(10) Patent No.: US 12,751,831 B2
(45) Date of Patent: Oct. 6, 2026

(54) METHODS AND APPARATUSES FOR TRIALING A HUMERAL HEAD

(71) Applicant: Zimmer, Inc., Warsaw, IN (US)

(72) Inventors: Donald W. Dye, Jr., Warsaw, IN (US); Peter Darrigan, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 585 days.

(21) Appl. No.: 18/038,614

(22) PCT Filed: Dec. 2, 2021

(86) PCT No.: PCT/US2021/061625

§ 371 (c)(1),
(2) Date: May 24, 2023

(87) PCT Pub. No.: WO2022/120060

PCT Pub. Date: Jun. 9, 2022

(65) Prior Publication Data

US 2023/0310166 A1 Oct. 5, 2023

Related U.S. Application Data

(60) Provisional application No. 63/121,018, filed on Dec. 3, 2020.

(51) Int. Cl.

| | |
|---|---|
| ***A61F 2/40*** | (2006.01) |
| ***A61F 2/46*** | (2006.01) |
| *A61F 2/30* | (2006.01) |

(52) U.S. Cl.

CPC .... *A61F 2/4014* (2013.01); *A61F 2002/3009* (2013.01); *A61F 2002/30617* (2013.01);

(Continued)

(58) Field of Classification Search

CPC .......... A61F 2/4684; A61F 2002/30617; A61F 2002/3009; A61F 2/4014; A61F 2002/4037; A61F 2002/4044

See application file for complete search history.

(56) References Cited

U.S. PATENT DOCUMENTS

| | | | |
|---|---|---|---|
| 6,673,114 | B2 | 1/2004 | Hartdegen et al. |
| 6,736,852 | B2 | 5/2004 | Callaway et al. |

(Continued)

FOREIGN PATENT DOCUMENTS

| | | |
|---|---|---|
| CN | 101184457 | 5/2008 |
| CN | 104684507 | 6/2015 |

(Continued)

OTHER PUBLICATIONS

"International Application Serial No. PCT/US2021/061625, International Search Report mailed May 3, 2022", 8 pgs.

(Continued)

*Primary Examiner* — Javier G Blanco

(74) *Attorney, Agent, or Firm* — SCHWEGMAN LUNDBERG & WOESSNER, P.A.

(57) ABSTRACT

Apparatuses, systems and methods such as a trial apparatus for selecting a position of a prosthetic head component on a humerus are disclosed. The trial apparatus can optionally include a body (36) and a thimble (38). The body can have a plurality of indicia (46) and can form a portion of a joint (37). The thimble can be couplable to the body via the joint. The thimble can be rotatable relative to the body via the joint and can include one or more indicia (62) for use with the plurality of indicia of the body. The thimble can be mountable to a prosthetic stem (30) implanted in the humerus.

10 Claims, 14 Drawing Sheets

(52) U.S. Cl.
CPC ................. *A61F 2002/4037* (2013.01); *A61F 2002/4044* (2013.01); *A61F 2/4684* (2013.01)

(56) References Cited

U.S. PATENT DOCUMENTS

| | | | | |
|---|---|---|---|---|
| 7,431,736 | B2 | 10/2008 | Maroney et al. | |
| 8,647,387 | B2 | 2/2014 | Winslow | |
| 2001/0053935 | A1 | 12/2001 | Hartdegen et al. | |
| 2002/0120339 | A1* | 8/2002 | Callaway | F16C 11/106 623/23.47 |
| 2011/0035015 | A1* | 2/2011 | Stone | A61F 2/4014 623/19.14 |
| 2011/0060418 | A1 | 3/2011 | Bailey et al. | |
| 2016/0030187 | A1 | 2/2016 | Sperling et al. | |
| 2016/0287400 | A1* | 10/2016 | Muir | A61F 2/4014 |
| 2018/0092760 | A1* | 4/2018 | Sperling | A61F 2/4684 |

FOREIGN PATENT DOCUMENTS

| | | | |
|---|---|---|---|
| CN | 204931906 | | 1/2016 |
| CN | 116456939 | | 7/2023 |
| EP | 2668930 | A1 | 12/2013 |
| EP | 4255354 | | 3/2025 |
| WO | WO-2020072465 | A2 | 4/2020 |
| WO | WO-2022120060 | A1 | 6/2022 |

OTHER PUBLICATIONS

"International Application Serial No. PCT/US2021/061625, Invitation to Pay Additional Fees mailed Mar. 9, 2022", 11 pgs.

"International Application Serial No. PCT/US2021/061625, Written Opinion mailed May 3, 2022", 9 pgs.

"International Application Serial No. PCT US2021 061625, International Preliminary Report on Patentability mailed Jun. 15, 2023", 11 pgs.

"European Application Serial No. 21845130.0, Response to Communication Pursuant to Rules 161 and 162 EPC filed Dec. 20, 2023", 17 pgs.

"Chinese Application Serial No. 202180076998.1, Office Action mailed Mar. 9, 2026", w English Translation, 21 pgs.

* cited by examiner

METHODS AND APPARATUSES FOR TRIALING A HUMERAL HEAD

CLAIM OF PRIORITY

This application is a U.S. National Stage Application under 35 U.S.C. 371 from International Application Serial No. PCT/US2021/061625, filed on Dec. 2, 2021, and published as WO 2022/120060 A1 on Jun. 9, 2022, which claims the benefit of U.S. Provisional Patent Application Ser. No. 63/121,018, filed on Dec. 3, 2020, the benefit of priority of each of which is claimed hereby, and each of which is incorporated by reference herein in its entirety.

TECHNICAL FIELD

This document pertains generally, but not by way of limitation, to apparatuses and methods for performing arthroplasty procedures. More particularly, this disclosure relates to, but not by way of limitation, intra-operative planning techniques for selecting the position of a prosthetic device component for a patient into which the prosthetic device component will be implanted.

BACKGROUND

A shoulder joint comprises the juncture of the scapula, the clavicle and the humerus. The head of the humerus fits into a shallow socket of the scapula called the glenoid fossa to form a mobile joint. When the joint is articulated, the humeral head moves in the glenoid fossa to provide a wide range of motion. The shoulder joint may suffer from various maladies including rheumatoid arthritis, osteoarthritis, rotator cuff arthropathy, avascular necrosis, bone fracture or failure of previous joint implants. If severe joint damage occurs and no other means of treatment is found to be effective, then shoulder reconstruction may be necessary.

A shoulder joint prosthesis generally includes the replacement of the ball (glenosphere) of the humerus and, optionally, the socket (glenoid) of the shoulder blade with specially designed artificial components. The bio-kinematics, and thus the range of motion in the shoulder vary greatly among prospective patients for reconstruction shoulder surgery. The humeral component typically can have a metal shaft or stem with a body portion that can be embedded in the resected humerus and a generally hemispherical head portion supported on the stem. The head portion can slidingly engage a glenoid implant on the glenoid fossa. During reconstructive surgery, the components of the prosthesis can be matched with the bio-kinematics of the patient in an effort to maintain the natural range of motion of a healthy shoulder joint. Thus, a shoulder prosthesis design can be readily adaptable to a wide range of bio-kinematics for prospective patients.

In this regard, shoulder prostheses are generally available as either unitary structures or modular components. With unitary shoulder prosthesis, a large inventory of differently sized prostheses must sometimes be maintained to accommodate the different bone sizes and joint configurations of the prospective patients. With such unitary shoulder prosthesis, the patient can typically be evaluated by X-ray to determine approximate sizes of prostheses needed for reconstruction. A number of differently sized prostheses can be selected as possible candidates based upon this preliminary evaluation. Final selection of the appropriately sized prosthesis can be made during the surgery. With unitary shoulder prosthesis, each design can represent a compromise that is unable to achieve all of the natural range of motion of a healthy shoulder joint because of the fixed geometric configuration in their design.

Modular prostheses systems that can reduce the need to maintain large inventories of various sized components are known in the art. Conventionally, a humeral prosthesis can include two components: a humeral stem component and a spherical head releasably coupled to the stem. Alternatively, a three component design is known in which the stem and spherical head are interconnected with an adapter. In either of the two-piece or three-piece designs, a radial offset or angulator inclination of the head relative to the stem can be provided in individual components. Different radial offsets or angular inclinations are achieved through the use of different adapters or heads. In this regard, conventional modular shoulder prosthesis kits can include multiple components such as adapters and heads to achieve a range of prosthetic options.

While providing an advantage over the unitary design in reducing the number of components needed, an inventory of head components and/or adapter components must sometimes be maintained to provide the desired range of geometric configurations with the conventional modular shoulder prostheses. These components can be readily adaptable to provide a range of geometric configurations, i.e. radial offsets of angular inclination while minimizing the number of components required.

Examples of humeral head trialing devices are described in U.S. Pat. No. 8,647,387 to Winslow, U.S. Pat. No. 7,431,736 to Maroney et al., U.S. Pat. No. 6,736,852 to Callaway et al., U.S. Pat. No. 6,673,114 to Hartdegen et al., and U.S. Pub. No. 2016/0030187 to Sperling et al.

OVERVIEW

The present inventors have recognized, among other things, that a problem to be solved relates to the need for surgeons to have to select a desired position (i.e. location and orientation) of a humeral head and a corresponding humeral head trial. This process can be complex and can involve the movement of several components that are intricately attached to each other, marking of bone in several locations, cross-referencing different types of indicia on the humeral head and on the humeral head trial, cross-referencing various other criteria (e.g., bone coverage, location of a top dead center, location of a maximum offset, etc.) in order to properly position the humeral head for the shoulder prosthesis. Because of the complexity involved, the surgeon can be left with making an informed estimate of the desired humeral trial position when positioning the humeral head prosthesis. Thus, translating the position of the humeral head trial to that of the humeral head may not always be accurately performed.

The present subject matter can help provide a solution to various problems associated with the trialing of a humeral head by providing a trialing apparatus that can be configured to couple directly to a humeral stem. The trialing apparatus can also be positionally adjustable (relative to bone and the humeral stem) in a manner similar to that of the humeral head and stem adaptor. The trialing apparatus can include indicia that are the same as or very similar to those of the humeral head and stem adaptor. These indicia can be more widely spaced apart so incremental sizes can be easier to achieve. The configuration of the trialing apparatus makes selecting a proper location of the humeral head and stem adaptor easier and more intuitive. Furthermore, the present subject matter contemplates that one or more components of the trialing apparatus can be transparent or translucent. This allows one or more indicia on a bone facing side of the trialing apparatus to be visible to the surgeon during adjusting of a relative position between components of the trial apparatus. This enhanced visibility also allows the surgeon to adjust positions and mark the bone more accurately with reference to the one or more indicia.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
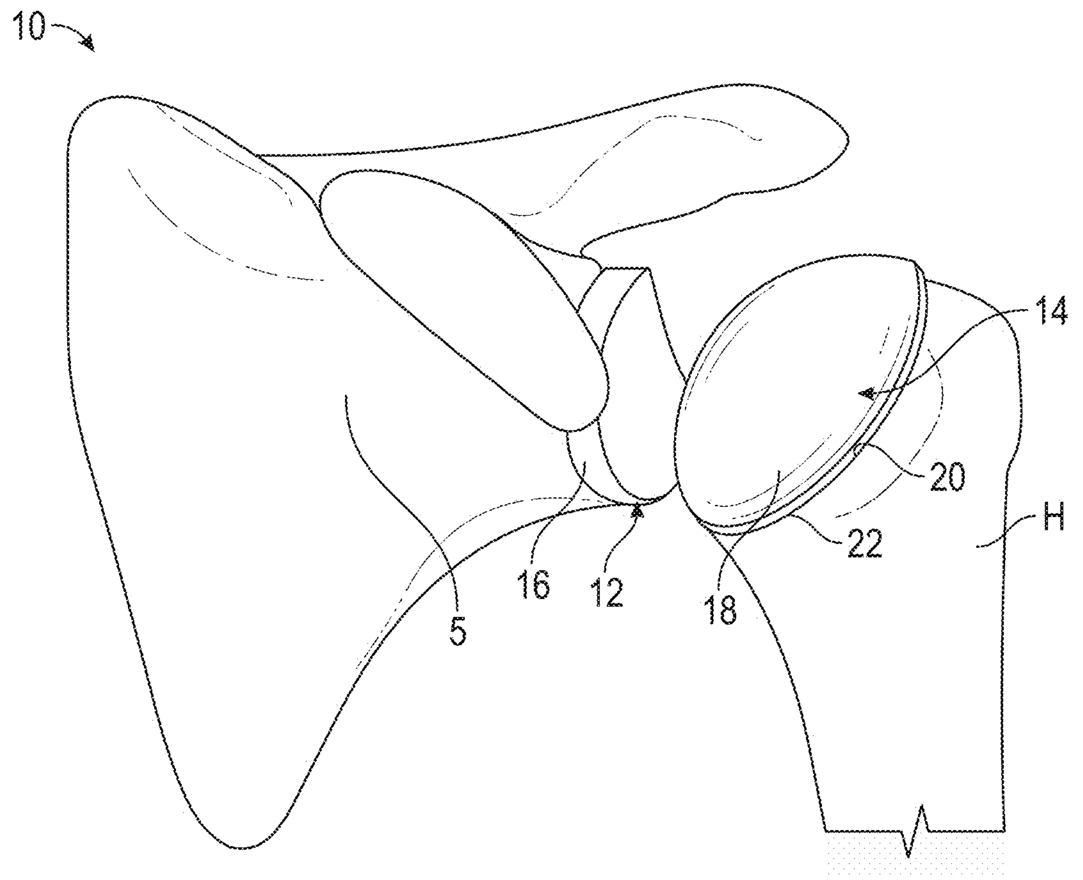
FIG. 1 is a front perspective view of a total shoulder arthroplasty system in which a humerus bone includes a humeral head component according to an example of the present application.
Figure 5:
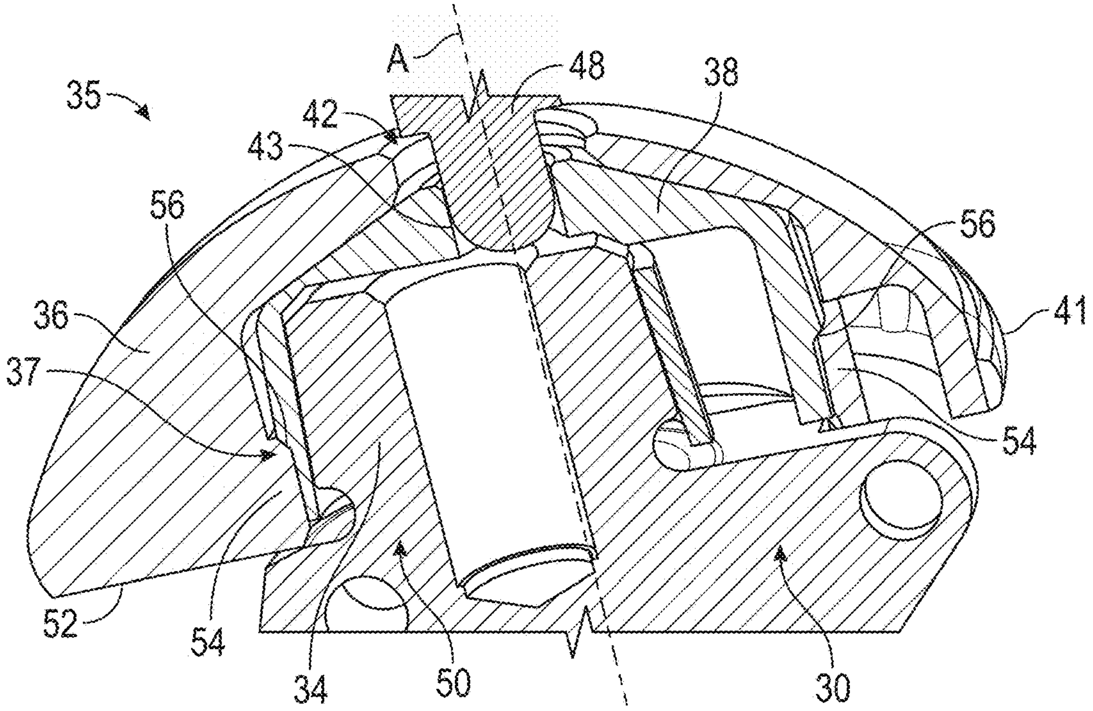
FIG. 5 is a cross-sectional view of the humeral trial apparatus of FIG. 4 mounted to one of the humeral stems of FIG. 2 according to an example of the present application.

FIG. 1 is a perspective view of a total shoulder arthroplasty system 10 comprising implanted a prosthetic glenoid 12 and an implanted humeral head prosthetic system 14. The prosthetic glenoid 12 can include a glenoid 16 and humeral head prosthetic system 14 can include a humeral head 18. The glenoid 16 can be secured to scapula bone S using any suitable means, such as a center post and a plurality of peripheral posts. The humeral head 18 can be secured to humerus bone H via a stem adaptor 24 (FIGS. 11C and 11D) that connects to the humeral head 18 and to a humeral stem 30 (FIGS. 2, 3 and 5).

The scapula bone S and the humerus bone H are typically reamed, resected or otherwise prepared to receive the glenoid 16 and the humeral stem 30.

As can be seen in FIG. 1, the humeral head 18 can be mounted to humerus bone H such that the perimeter 20 of humeral head 18 can be substantially aligned with edge 22 of humerus bone H. It can be desirable for the humeral head 18 to be properly centered on humerus bone H to achieve correct anatomic operation, for example, so that the humeral head 18 can smoothly rotate against glenoid 16. As such, the position and size of the humeral head 18 can be selected so that the diameter of perimeter 20 substantially matches that of edge 22. As described previously, it can be a complex process for the humeral head 18 to be optimally aligned with edge 22 upon implantation. As such, the present disclosure provides a system, apparatus and method for trialing, positioning and aligning the humeral head 18 with the humerus bone H.

Figure 2:
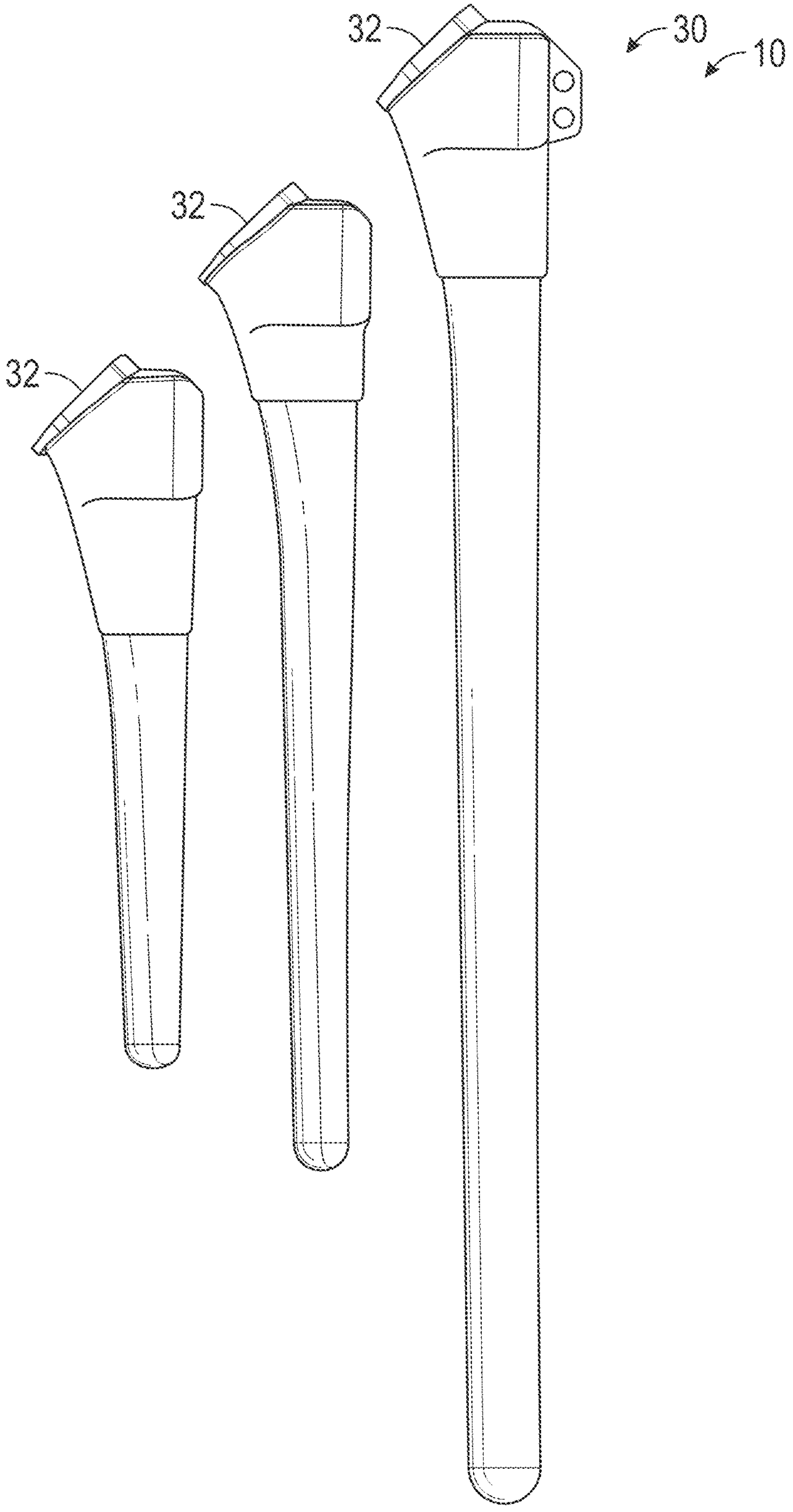
FIG. 2 is a schematic illustration of a plurality of a humeral stems that can be used with the total shoulder arthroplasty system according to an example of the present application.
Figure 3:
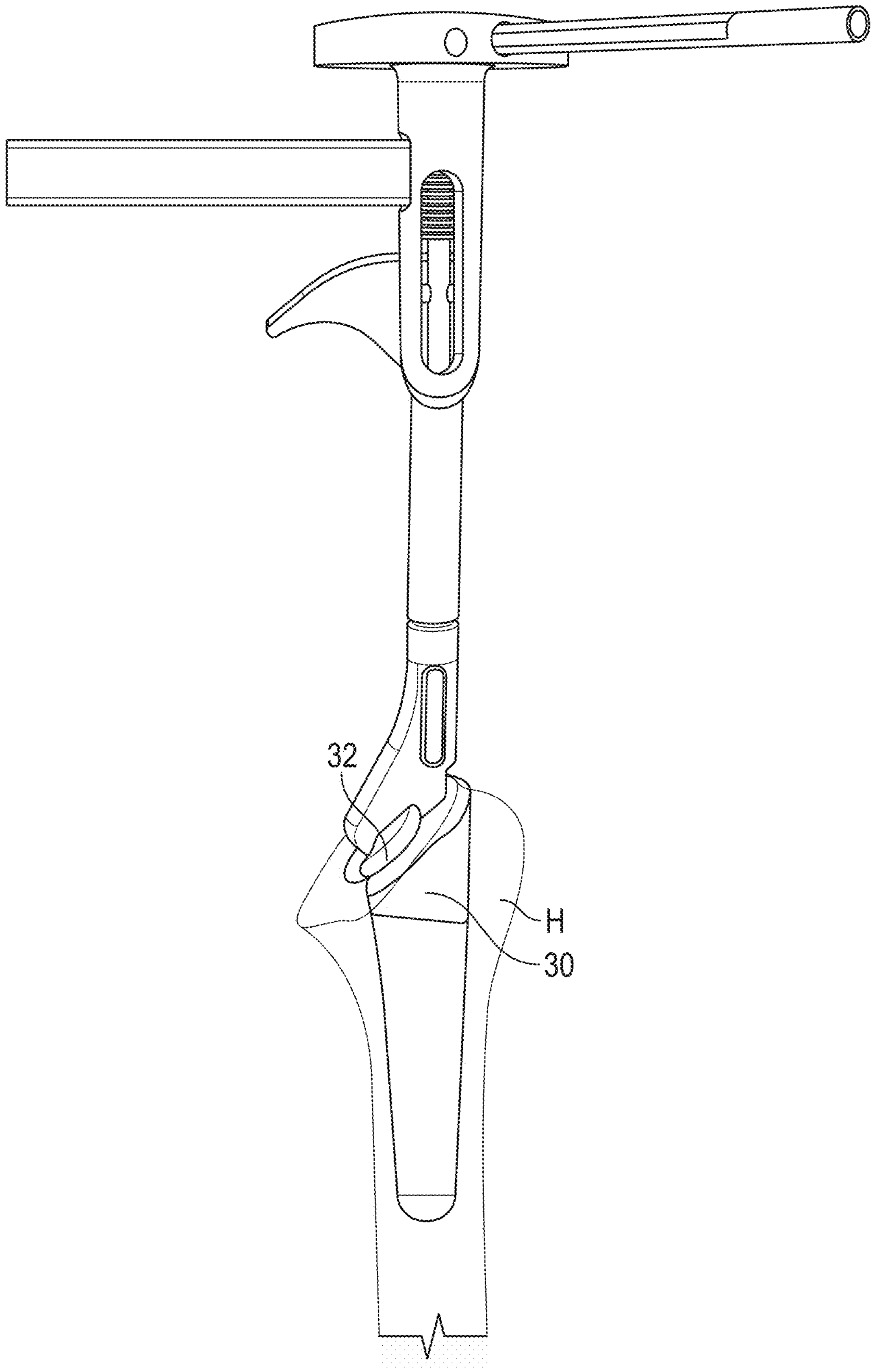
FIG. 3 is a perspective view of one of the plurality of humeral stems being placed into a recess in the humerus according to an example of the present application.

FIG. 2 is a schematic illustration of a plurality of the humeral stems 30 that can be used with the total shoulder arthroplasty system 10. The humeral stems 30 are available in different sizes and lengths as necessary based upon patient factors such as bone size and bone quality. The humeral stems 30 can optionally include different stem lengths, can have portions coated or otherwise formed of porous material to facilitate bony ingrowth. Each of the humeral stems 30 can include a proximal end 32.

As shown in FIG. 3, the proximal end 32 can protrude slightly from or be flush with the glenoid surface of the humerus bone H when the humeral stem 30 is positioned in the humerus bone H. Positioning of the humeral stem 30 into a reamed recess in the humerus bone H can be performed by an inserter or guide as shown in FIG. 3.

The proximal end 32 of the humeral stem 30 can include a trunnion 34 (FIG. 5), morse taper or other feature the facilitates connection of the humeral stem 30 to the stem adaptor 24 (FIGS. 11C and 11D), and hence, the humeral head 18 as shown in FIG. 1.

Figure 4:
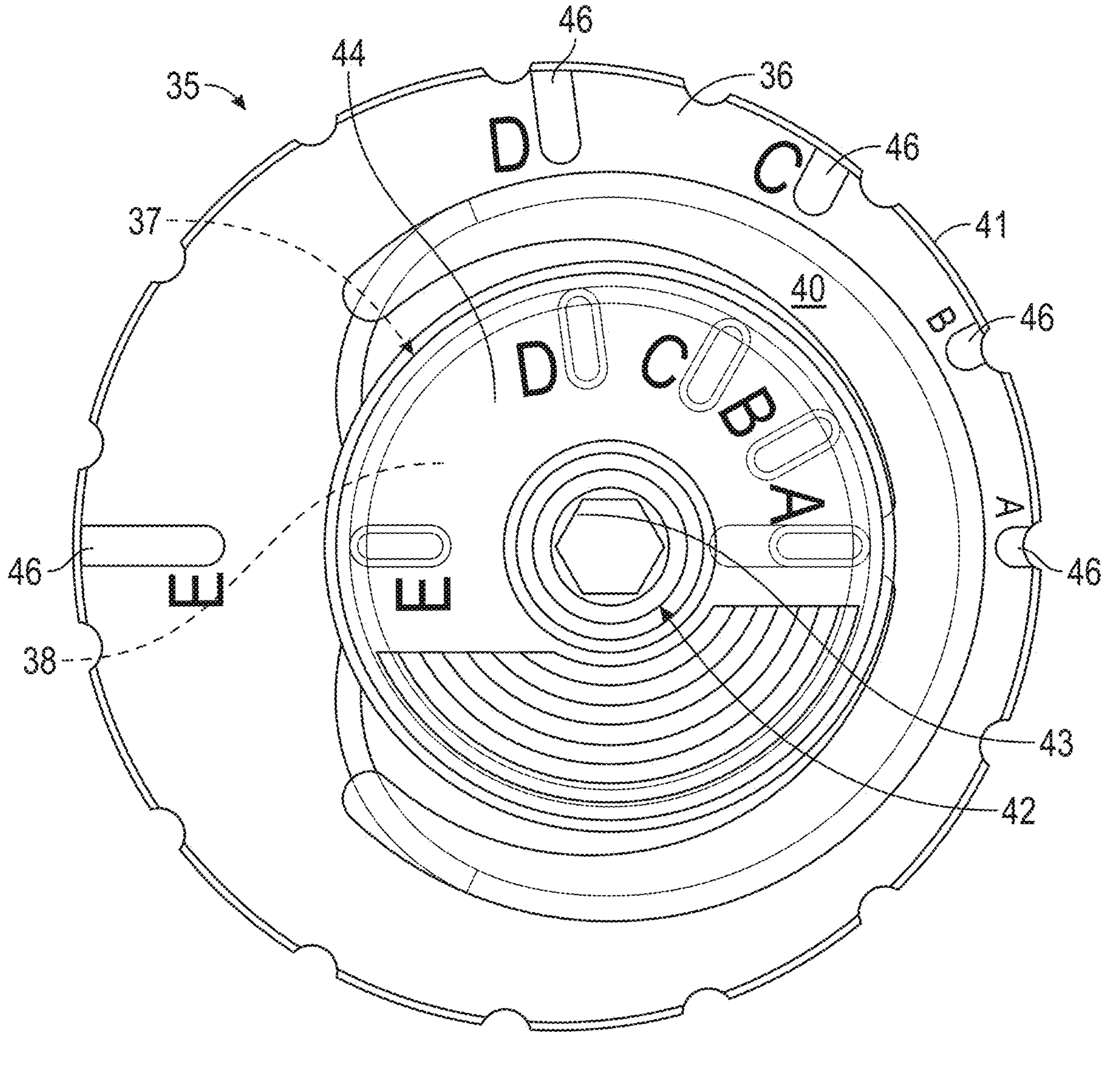
FIG. 4 is a front plan view of a humeral trial apparatus having a body and a thimble according to an example of the present application.

FIG. 4 shows a plan view of a front (i.e. surgeon facing or non-bone facing) of a humeral trial apparatus 35 according to one example. The humeral trial apparatus 35 can include a body 36 and a thimble 38. The body 36 and the thimble can be moveably connected relative to one another via a joint 37.

The body 36 can have a front surface 40 (sometimes referred to herein as a non-bone facing surface, proximal surface or top surface). The body 36 can be puck shaped, dome or hemispherical shaped according to some examples. The front surface 40 can terminate at a perimeter 41 of the body 36. The body 36 can be circular in cross-section and can have a size and shape similar to that of the humeral head 18 (FIG. 1).

As shown in FIG. 4, the body 36 can have a recess 42 forming an opening in the front surface 40. This opening can provide access, via the recess 42, to a proximal end of the thimble 38 when the thimble 38 is inserted in and captured by the body 36 as shown in FIG. 4. The proximal end of the thimble 38 can have a head 43, recess or other feature that can be engaged (via the recess 42) with a driver (shown in FIGS. 5 and 7A). The driver can engage or otherwise couple with the thimble 38 to rotate the thimble 38 relative to the body 36 (and/or the humeral stem) as further described herein.

According to the example of FIG. 4, a portion 44 of the body 36 that can include all or part of the body 36 can be transparent or translucent. This can facilitate the surgeon being able to view the position of the thimble 38, for example. The body 36 can include a plurality of indicia 46. The plurality of indicia 46 can be on one or more of the front surface 40, can be within a recess of the body as further illustrated in FIG. 6, and/or can be on an opposing bone facing surface from the front surface 40. The plurality of indicia 46 can be circumferentially arranged along or adjacent the perimeter 41 and can be arranged circumferentially around a centerline axis A of the body 36 as shown in FIG. 5.

FIG. 5 shows the humeral trial apparatus 35, in particular the thimble 38, mounted to the trunnion 34 of the humeral stem 30. As shown in FIG. 5, the thimble 38 is configured to rotate (via the joint 37) to adjust a position of the body 36 relative to the prosthetic stem 30. To this end, FIG. 5 shows a driver 48 engaging the head 43 of the thimble 38 to facilitate the rotation of the thimble 38 relative to the body 36 and/or the humeral stem 30. Put another way, the driver 48 can rotate the thimble 38 relative to the body 36 and can also be used to rotate the body 36 and thimble 38 relative to the humeral stem 30.

Figure 6:
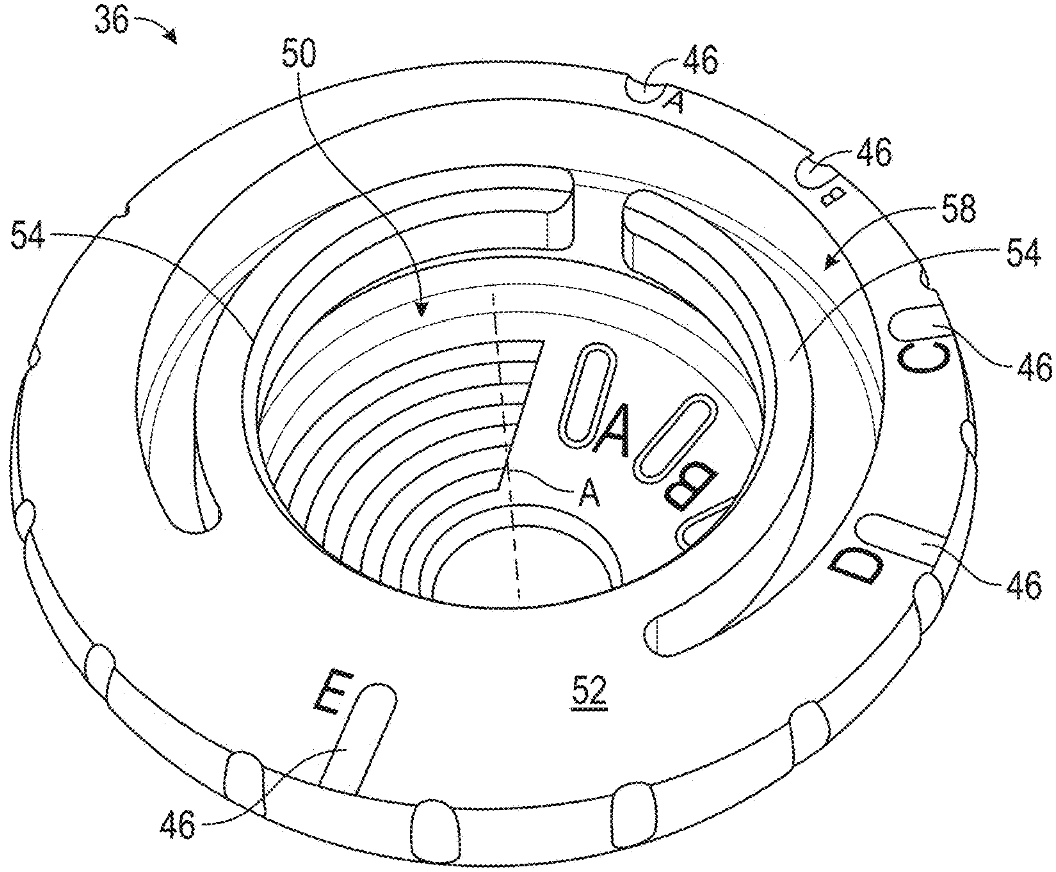
FIG. 6 is a perspective view of a bone facing side of the body of the humeral trial apparatus of FIGS. 4 and 5.

FIGS. 5 and 6 illustrate a recess 50 (part of joint 37) within the body 36. This recess 50 can be configured (sized and shaped) to receive the thimble 38. The recess 50 can have an opening on a distal surface 52 (also referred to herein as a bone interfacing surface or stem facing surface) of the body 36 and can communicate with the recess 42 at a proximal portion.

FIG. 5 shows the hemisphere shape of the body 36 extending from the perimeter 41 to a domed peak that can be located at the centerline axis A of the body 36. The recess 42 can be located at the domed peak, can oppose the recess 50 and can communicate with the recess 50. In FIG. 5, the thimble 38 is illustrated received in the recess 50 and can be rotatably captured by the body 36 in a snap-fit engagement. As show in FIGS. 5 and 6, a portion of the recess 50 can be formed by the one or more fingers 54.

The snap-fit engagement can be facilitated by the one or more fingers 54 of the body 36. The thimble 38 along the perimeter 41 can have a larger proximal diameter and then a smaller distal diameter. This change in diameter can form a lip 56 on the thimble 38. The lip 56 can have a chamfer of about 30 to 40 degrees between the larger diameter proximal portion and the smaller diameter distal portion. These fingers 54 (also illustrated in FIG. 6) can be figured to elastically deform slightly outward to receive the thimble 38. As shown in FIG. 5, the fingers 54 can have chamfers, projections or other features configured to engage with mating features (e.g., a chamfer or lip 56) of the thimble 38 when the thimble 38 is fully inserted in the recess 50. The lip 56 can be configured to be engaged by the one or more fingers 54 when the thimble 38 is inserted in the recess 50. This engagement can retain the thimble 38 within the body 36 but can allow the thimble 38 to be rotated relative to the body 36, for example.

FIG. 6 shows the body 36 with the thimble 38 removed to better illustrate the recess 50 and the one or more fingers 54. The distal surface 52 can be substantially flat and can include some or all of the plurality of indicia 46, for example. As shown in FIG. 6, some of the plurality of indicia 46 can also be located within the recess 50. As shown in FIG. 6, a recess 58 can be located outward (as measured from centerline axis A) of the recess 50 and the one or more fingers 54. This recess 58 can allow the one or more fingers 50 to elastically flex outward as previously described to receive the thimble 38 (FIG. 4).

Figure 7A:
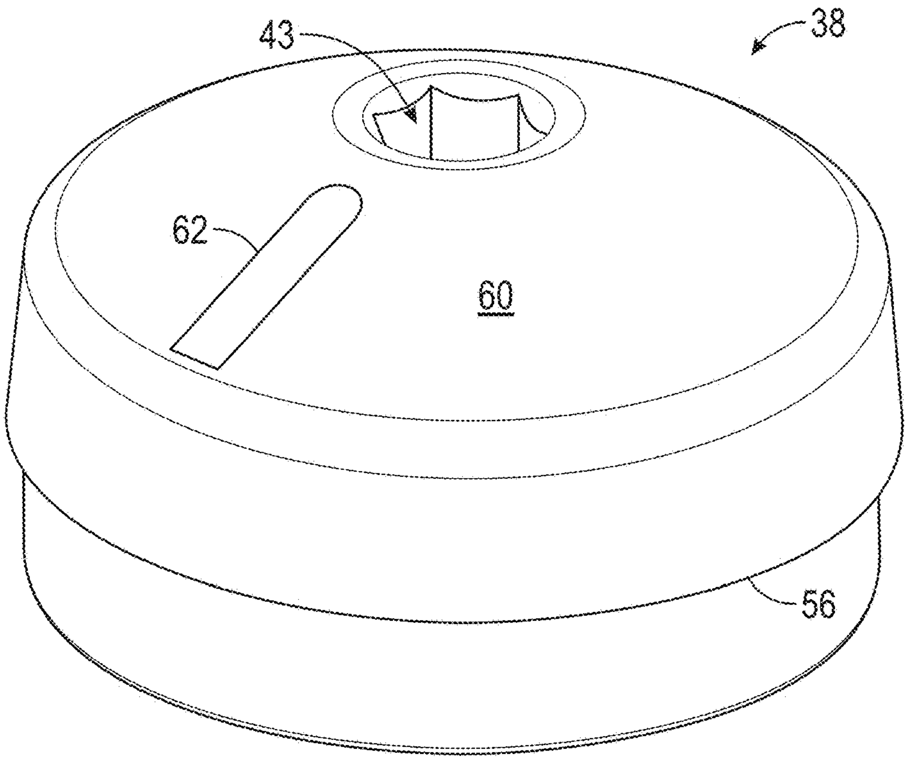
FIG. 7A is a perspective view of the thimble of the humeral trial apparatus of FIGS. 4 and 5.

FIGS. 7A-7D show the thimble 38 in further detail. The thimble 38 can include the lip 56 along a periphery thereof and the head 43 as previously described. The thimble 38 can include a proximal surface 60 and indicia 62 as shown in FIG. 7A. The proximal surface 60 can extend from a periphery of the thimble 38 to the head 43, for example. The indicia 62 can comprise a line or other marking on the proximal surface 62, for example.

Figure 7B:
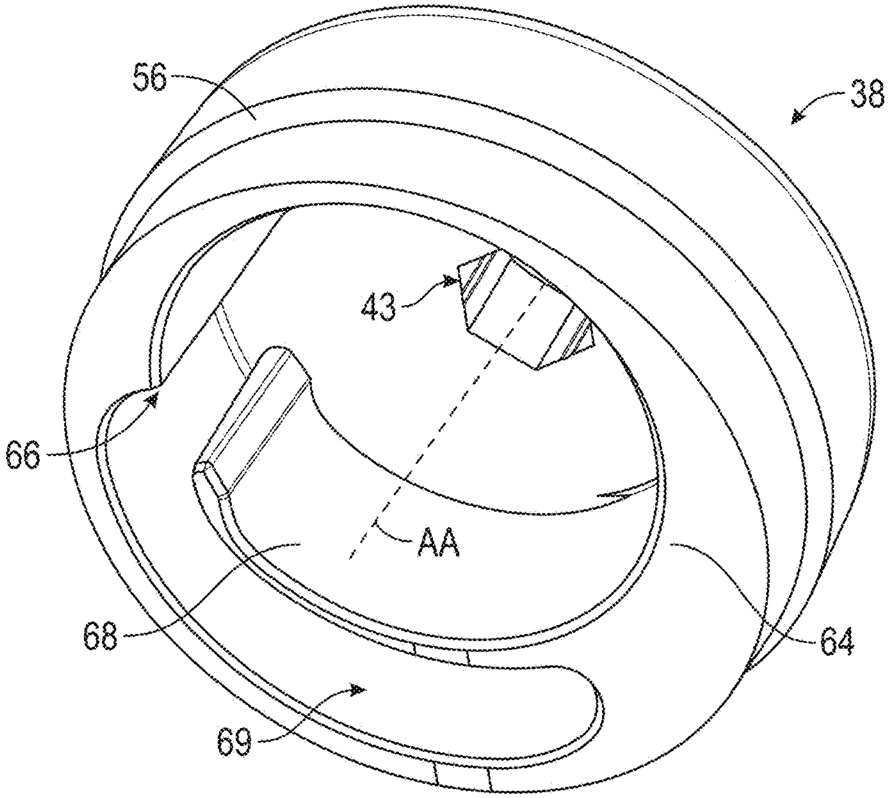
FIG. 7B is a second perspective view of the thimble of the humeral trial apparatus of FIGS. 4 and 5.
Figure 7C:
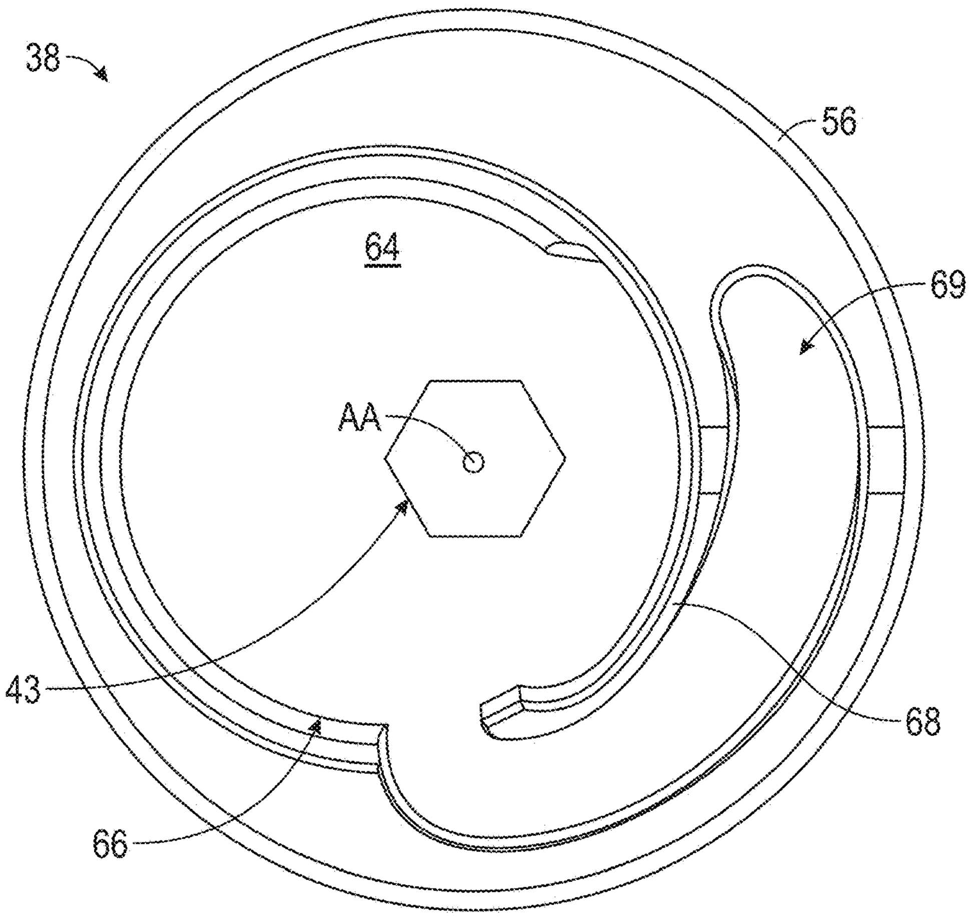
FIG. 7C is a plan view of the thimble of the humeral trial apparatus of FIGS. 4 and 5.
Figure 7D:
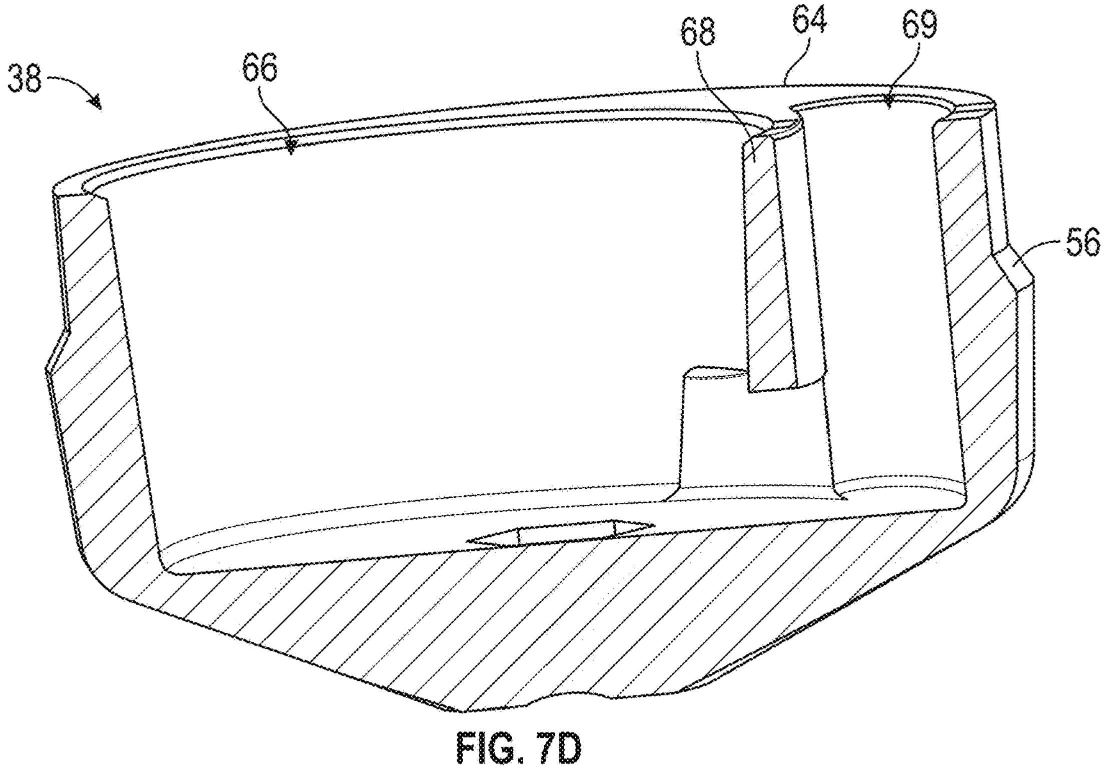
FIG. 7D is a cross-sectional view of the thimble of the humeral trial apparatus of FIGS. 4 and 5.

FIGS. 7B-7D show a distal side (also called a bone facing or stem facing side) of the thimble 38. The thimble 38 can include a distal surface 64, a recess 66, one or more fingers 68 and a recess 69.

As shown in FIGS. 7B-7D, the distal surface 64 can be substantially flat and can oppose the proximal surface 62. The recess 66 can have an opening at the distal surface 64. The recess 66 can extend proximally from the distal surface 64 to terminate adjacent or can communicate with the head 43, as shown in FIGS. 7B and 7C. The recess 66 can be offset from a centerline axis AA (FIGS. 7B and 7C) and/or the head 43 of the thimble 38. This offset can provide for adjustment of the position of the body 36 relative to the humerus bone as previously discussed and further illustrated herein.

The recess 66 can be partially formed by the one or more fingers 68. The one or more fingers 68 can be configured to elastically deflect outward toward recess 69 when the recess 66 receives the trunnion 34 of the humeral stem 30. The one or more fingers 68 can be configured to create a friction fit, snap-fit or other type of engagement with the trunnion 34 (FIG. 5) as desired. This engagement can allow the thimble 38 to rotatably mount to the trunnion 34 as shown previously in FIG. 5. The recess 66 can be tapered in a manner to receive but also allow for removal of the thimble 38 from the trunnion 34.

Figure 8:
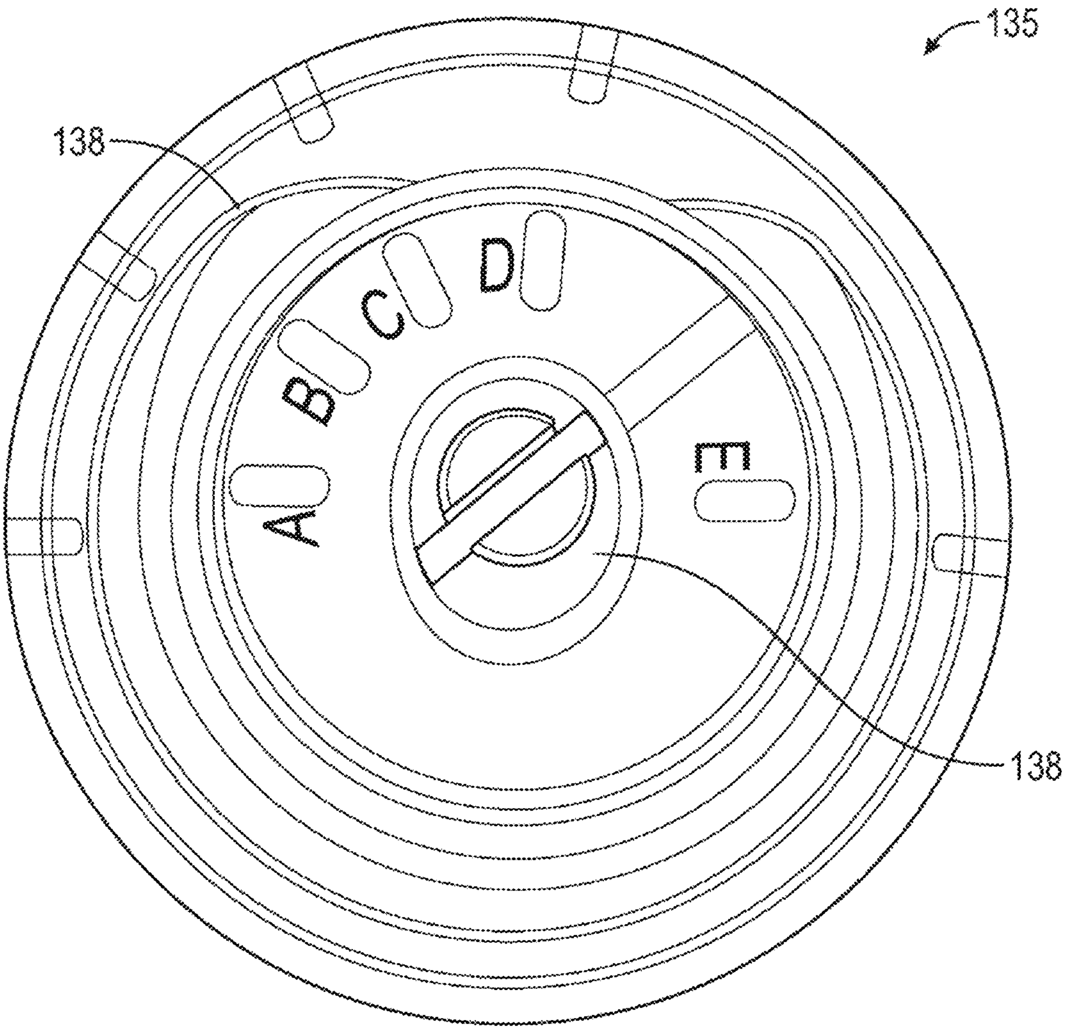
FIG. 8 is a front plan view of a humeral trial apparatus having a body and a thimble according to another example of the present application.
Figure 9:
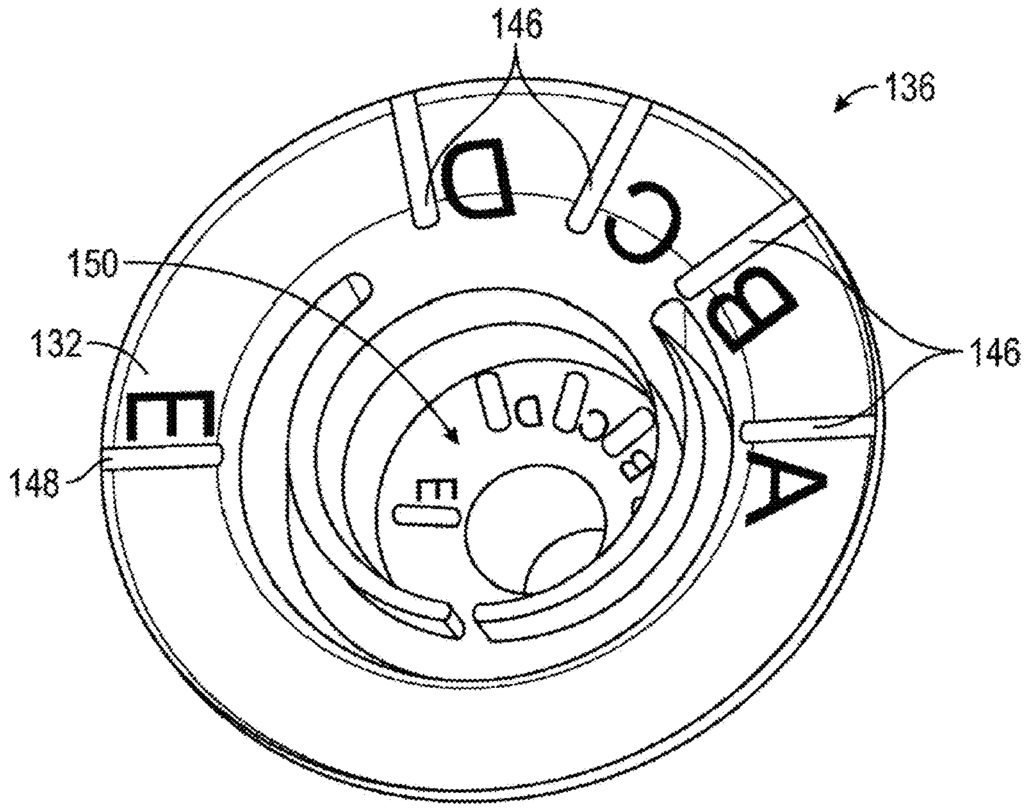
FIG. 9 is a perspective view of a bone facing side of the body of the humeral trial apparatus of FIG. 8.
Figure 10:
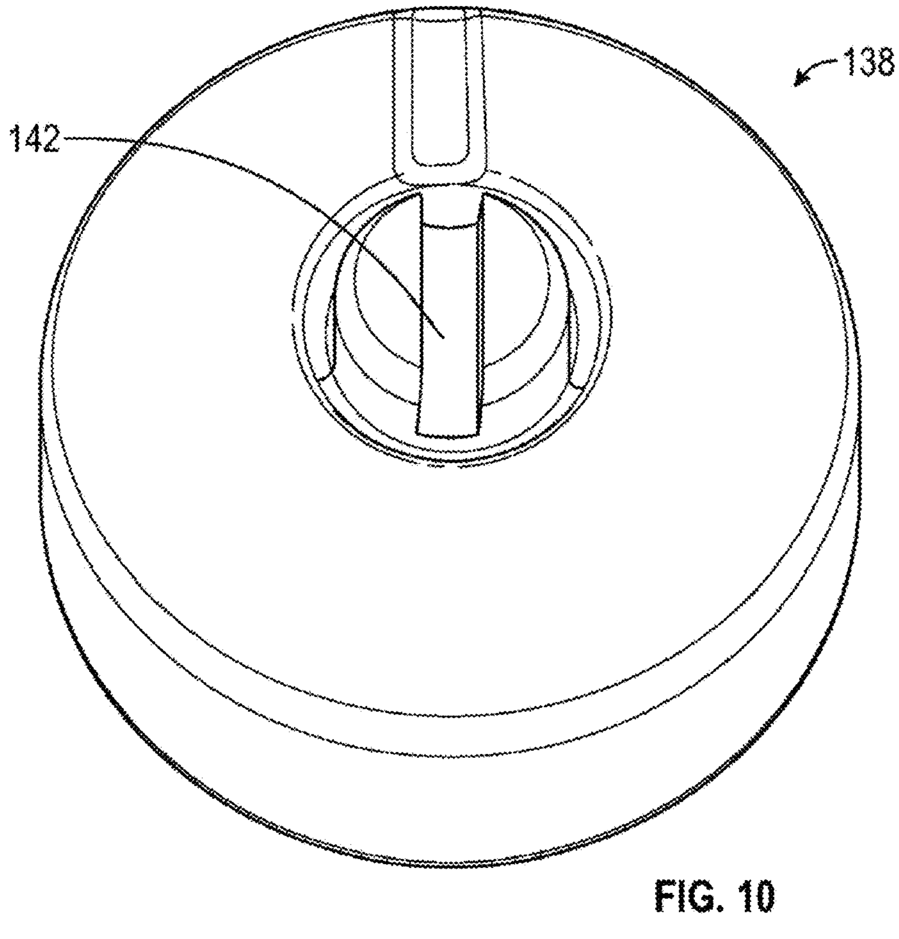
FIG. 10 is a perspective view of the thimble of the humeral trial apparatus of FIG. 8.

FIGS. 8-10 show another example of a humeral trial apparatus 135. The humeral trial apparatus 135 can be configured in the manner of the humeral trial apparatus 35 previously described. Thus, the humeral trial apparatus 135 can include a body 136 and a thimble 138. The body 136 can be comprised of a translucent or transparent material (e.g., polysulfone such as Radel® polyphenylsulfone (PPSU)) so as to be fully or partially see through for the surgeon. As shown in FIG. 9, due to this translucent or transparent material a plurality of indicia 146 can be located on a distal surface 152 and/or a recess 150 of the body 136 and can be visible through the body 136 from a side opposing the distal surface 152.

Thimble 138 can differ from the thimble 38 in that the head 43 can be a slot 142, for example. Thimble 138 can be made of any suitable biocompatible material (e.g., metal, metal alloy such as titanium or titanium alloy, polymer, etc.). Thimble 138 need not be translucent or transparent, although the thimble can be translucent or transparent according to some examples.

FIGS. 11A-11E show a method for positioning a prosthetic head component with a prosthetic stem relative to a bone. This method can be performed using one of the humeral trial apparatuses described and illustrated previously herein.

Figure 11A:
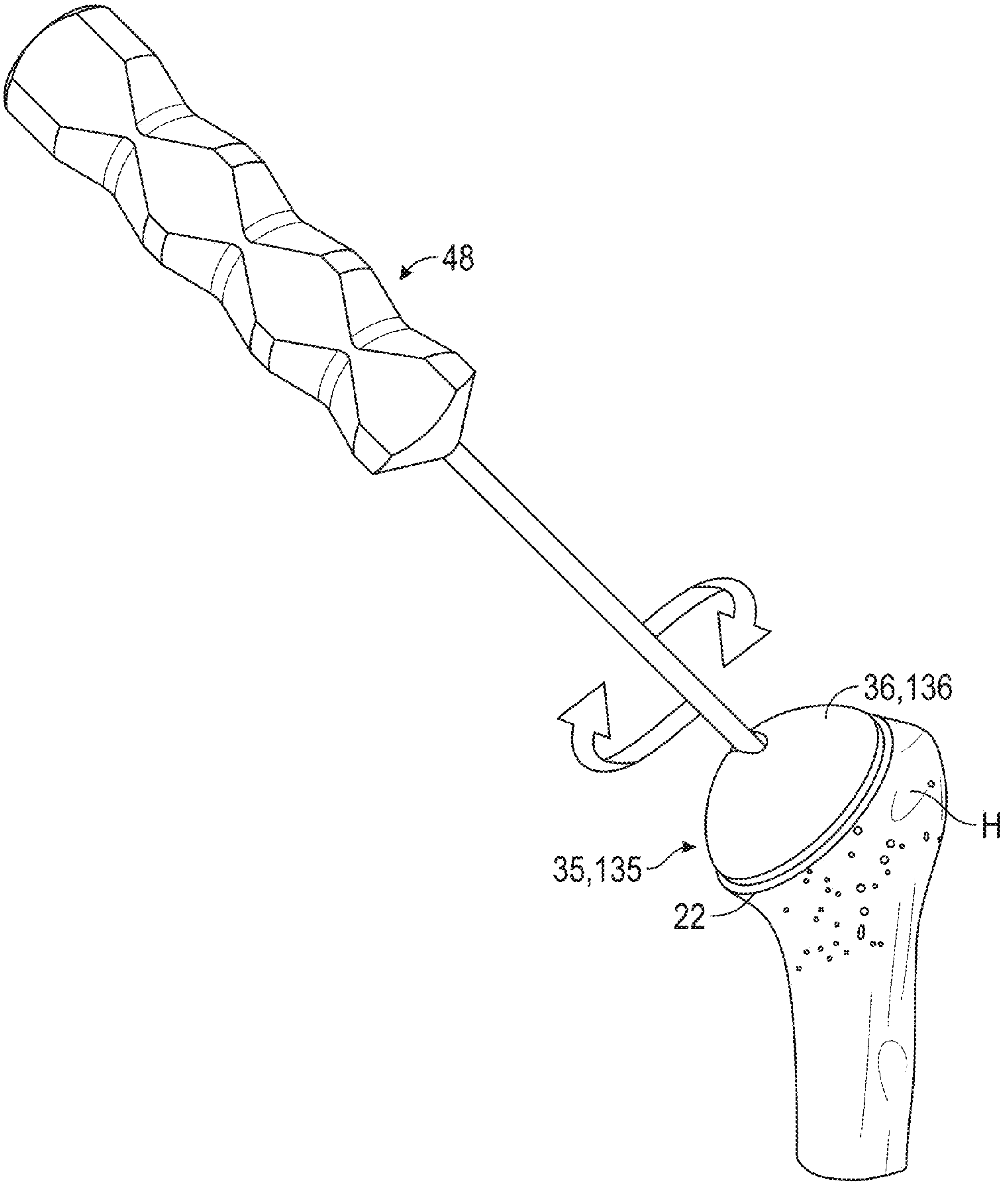
FIGS. 11A-11E show a method for positioning a prosthetic head component with a prosthetic stem relative to a bone using one of the humeral trial apparatuses described and illustrated herein.

FIG. 11A shows the driver 48 being utilized with one of the humeral trial apparatus 35 or 135. As shown in FIG. 11A, the driver 48 can be rotated to rotate the thimble relative to the body 36, 136 and the humeral stem (not shown). The surgeon may place a hand on the body 36, 136 during rotation of the thimble to discourage the body 36, 136 from co-rotating with the thimble. As discussed previously, the thimble 38, 138 can be rotated until a perimeter (e.g., perimeter 41) of the body 36, 136 substantially matches that of the edge 22 of the humerus bone H as shown in FIG. 11B.

Figure 11C:
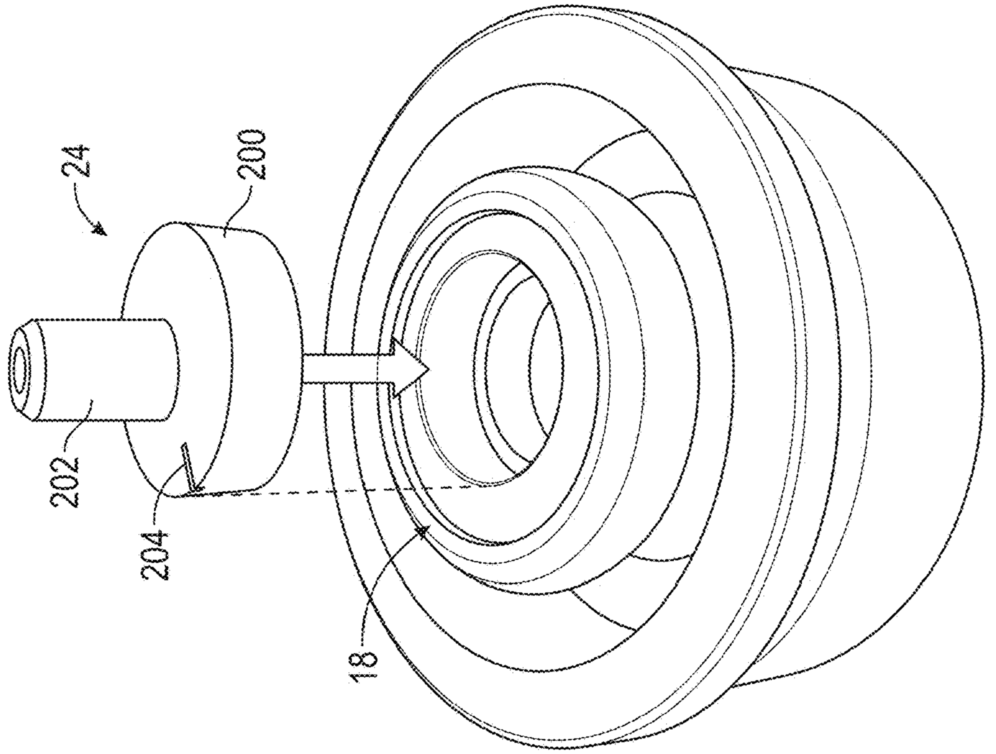
Figure 11B:
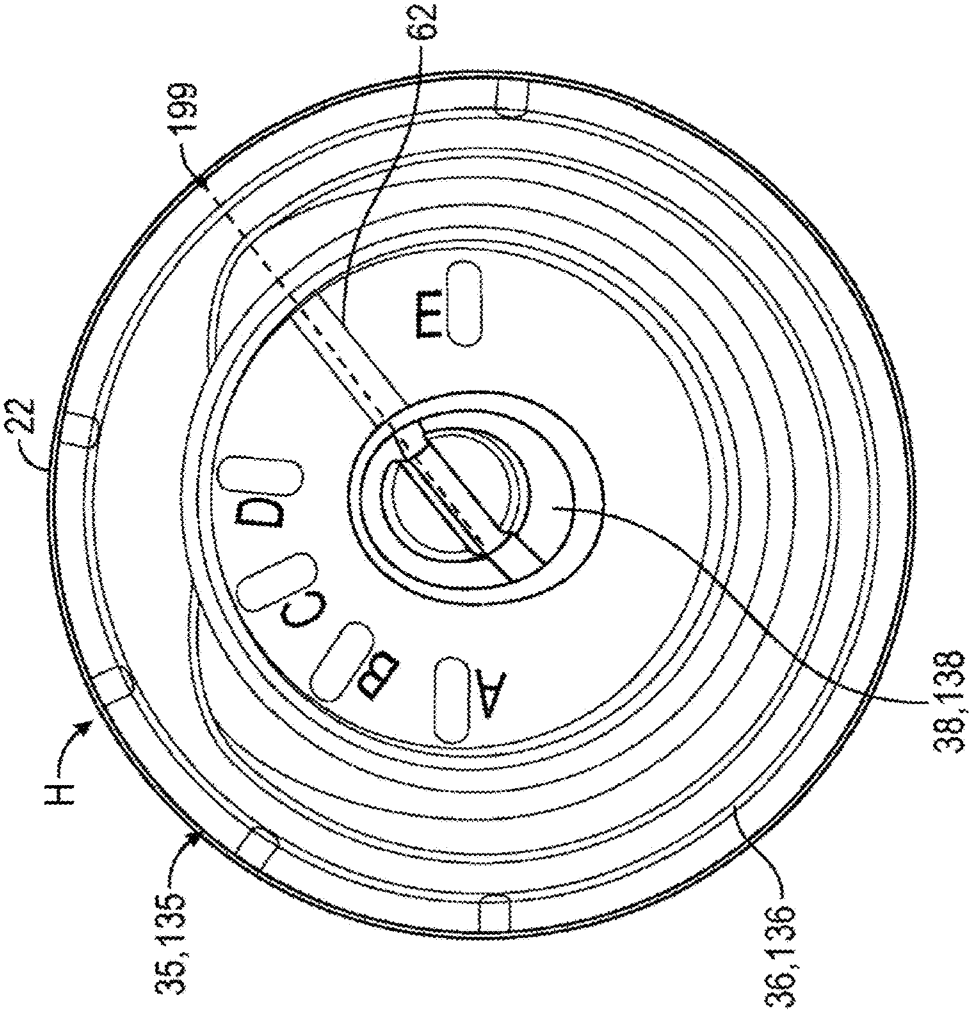

FIG. 11B shows the surgeon can start with the indicia 62 of the thimble 38, 138 aligned with the one of the indicia 46, 146 labeled "C". The thimble 38, 138 can then be rotated as shown in FIG. 11A to match the edge 22 of the humerus bone H. This can change the relative positions of the body 36, 136 and the thimble 38, 138. For example, the thimble 38, 138 can be rotated to the "D and ½" position shown in FIG. 11B. Optionally, an amount of maximum offset from the edge 22 can be determined and noted if desired. Once the desired position for the body 36, 136 on the bone is obtained, the indicia 62 of the thimble 38, 138 can be extrapolated linearly outward (indicated with dashed line in FIG. 11B) to the edge 22 and the bone (such as the edge 22) can be marked with a mark 199 as illustrated in FIG. 11B using known methods.

As shown in FIG. 11C, the humeral head 18 can be placed in into an impactor tray. The stem adapter 24 can have a body 200 configured to engage the humeral head 18. The stem adaptor 24 can have a neck 202 configured to engage the humeral stem 30 (FIGS. 2, 3 and 5).

Figure 11D:
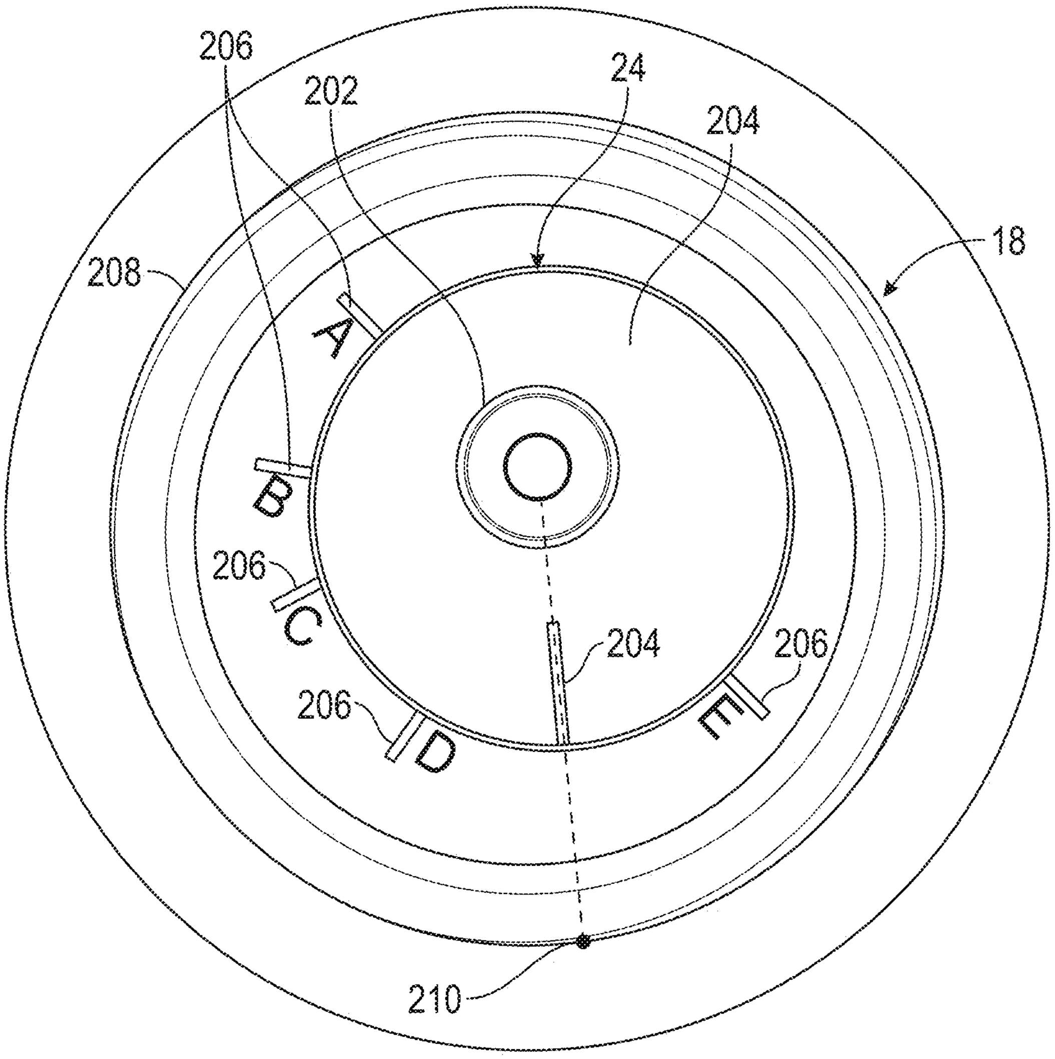

In FIGS. 11C and 11D, the stem adaptor 24 can be selected and can have an indicia 204 thereon. The indicia 204 can be configured in a similar or identical manner to the indicia 62 of the thimble 38, 138. For example, both can be lines. Similarly, the humeral head 18 can have a plurality of indicia 206. The indicia 204 can be used with the plurality of indicia 206 as shown in FIGS. 11C and 11D. The plurality of indicia 206 can be configured in a same or similar manner to the indicia 46, 146 of the body 36, 136. Thus, the plurality of indicia 206 can be identical to (i.e. each can be circumferentially arranged about a centerline axis of the humeral head 18, can be identically spaced and positioned, etc.) to the indicia 46, 146 of the body 36, 136. Put another way, the body 36, 136 can have the plurality of indicia 46, 146 configured in an identical manner to those of the plurality of indicia 206 of the humeral head 18. Thus, a relative position between the stem adaptor 24 and the humeral head 18 can be determined by replicating with the indicia 204 of the stem adaptor 24 and the plurality of indicia 206 of the humeral head 18, the relative positions of the thimble 38, 138 and the body 36, 136 as determined using the indicia 62 of the thimble 38, 138 and the plurality of indicia 46, 146 of the body 36, 136.

Figure 11E:
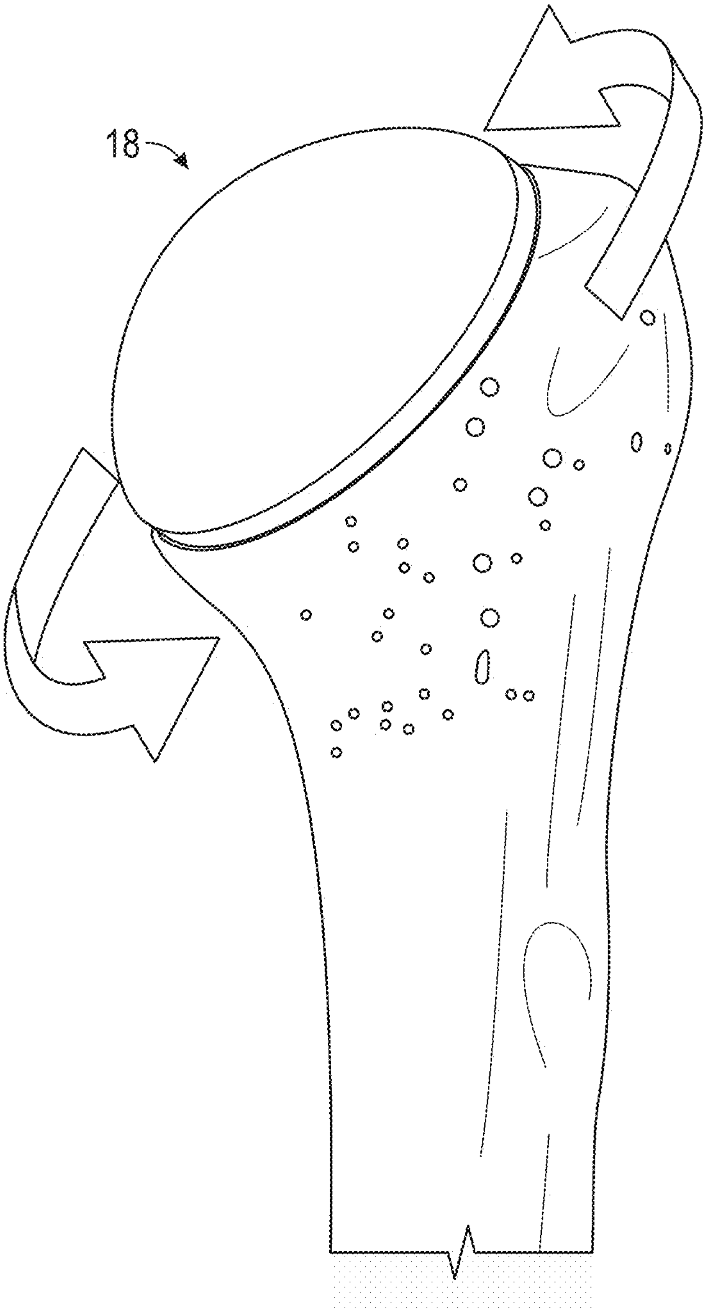

As shown in FIG. 11D, the indicia 204 can be extrapolated linearly outward (as indicated with dashed line) to a periphery 208 of the humeral head 18. A mark 210 can be made on the periphery in this location. In FIG. 11E, the humeral head 18 and the stem adaptor (not shown) can be adjusted to align the mark 210 with the mark 199 (FIG. 11B). Thus, the position of the stem adaptor and the humeral head on the humeral stem can be positioned to replicate the position of the body and thimble on the humeral stem.

Thus, the method of FIGS. 11A-11E can position the humeral head 18 with the prosthetic stem 30 relative to the humerus bone H. The method can include mounting the prosthetic stem to the bone, inserting the thimble within the body, mounting the thimble on the prosthetic stem, adjusting a relative position between the body and the thimble, marking the bone, recreating the relative position with a stem adaptor and the prosthetic head component; marking the prosthetic head component with the aid of an indicia on the stem adaptor once the recreating the relative position with the stem adaptor and the prosthetic head component is achieved, aligning the marking on the bone with the marking on the prosthetic head component, and attaching the prosthetic head component to the prosthetic stem via the stem adaptor.

Figure 12A:
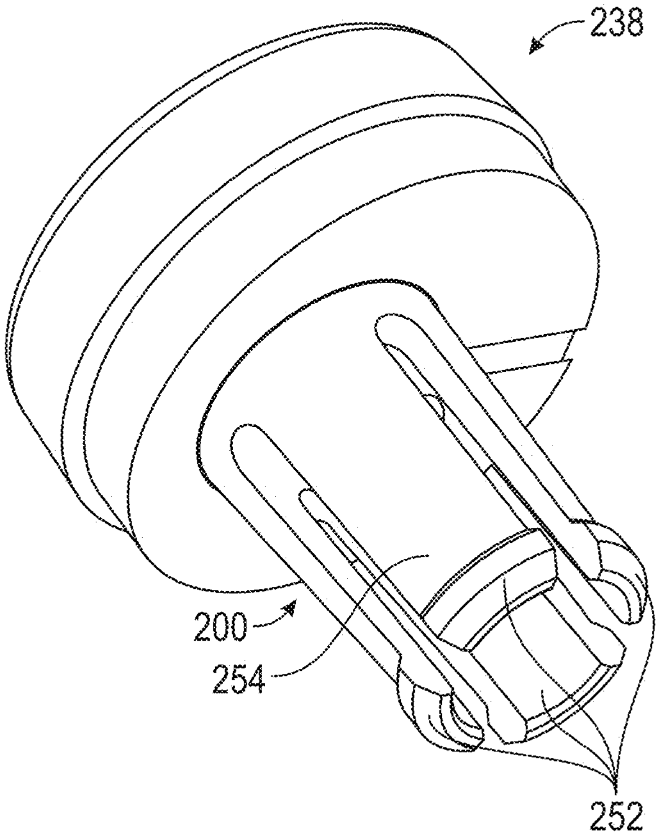
FIGS. 12A and 12B show perspective views of another example of a thimble of a humeral trial apparatus having a post as a connector.
Figure 12B:
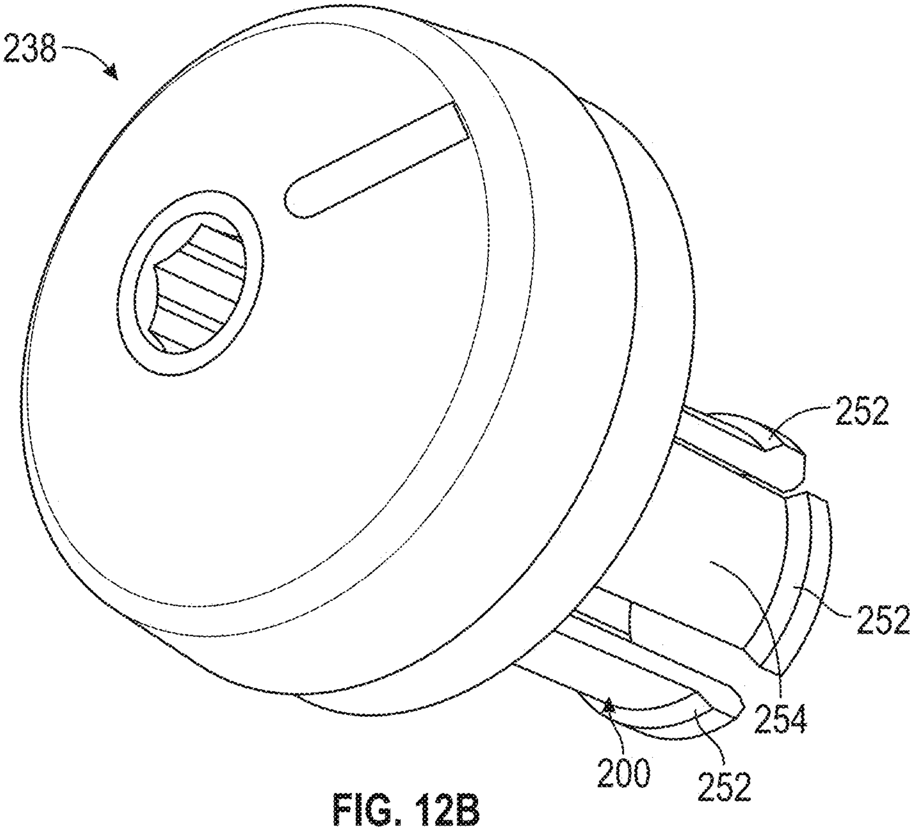

FIGS. 12A and 12B show a thimble 238 according to another example. The thimble 238 can differ from the thimble 38 or 138 previously illustrated in that the recess 66 can be replaced by a male feature such as a stem 200 having one or more flexible fingers 252 that define sidewalls 254 thereof. The stem 200 via the one or more flexible fingers 252, which can be separated by slots, can be configured to couple with the proximal head of the prosthetic stem in an adjustable manner as previously discussed. It is further recognized that according to further embodiments the body can include a male feature facilitating adjustable connection with the thimble, for example.

VARIOUS NOTES & EXAMPLES

Example 1 can include a trial apparatus for selecting a position of a prosthetic head component on a humerus. The trial apparatus can optionally include a body and a thimble. The body can have a plurality of indicia and can form a portion of a joint. The thimble can be couplable to the body via the joint. The thimble can be rotatable relative to the body via the joint and can include one or more indicia for use with the plurality of indicia of the body. The thimble can be mountable to a prosthetic stem implanted in the humerus.

Example 2 is the trial apparatus of Example 1, optionally the plurality of indicia can be arranged circumferentially about a centerline axis of the body.

Example 3 is the trial apparatus of any one or combination of Examples 1-2, optionally the body can comprise a hemisphere.

Example 4 is the trial apparatus of Example 3, optionally the plurality of indicia can be on a distal surface of the body and the body can be translucent such that the plurality of indicia are visible through the body from a side opposing the distal surface.

Example 5 is the trial apparatus of any one or combination of Examples 1-4, optionally the body can define a recess that comprises the portion of the joint, the thimble can be receivable by the recess, wherein the recess can be formed by one or more fingers, and wherein the fingers can be configured to elastically deform to retain the thimble in a snap-fit engagement.

Example 6 is the trial apparatus of Example 5, optionally the thimble can have a lip configured to be engaged by the one or more fingers when the thimble is inserted in the recess.

Example 7 is the trial apparatus of any one or combination of Examples 1-6, optionally the body includes a second recess opposing the joint, the second recess can communicates with the joint.

Example 8 is the trial apparatus of Example 7, optionally the thimble can include a head on a proximal end thereof, wherein, when the body and the thimble are assembled via the joint, the head can be accessible through the second recess of the body.

Example 9 is the trial apparatus of any one or combination of Examples 1-8, optionally the thimble includes one of a recess or a stem, and wherein a finger forms at least a portion of the recess or stem, and wherein the recess or stem of the thimble can be configured to elastically deform to retain the thimble on the prosthetic stem.

Example 10 is the trial apparatus of any one or combination of Examples 1-9, optionally the thimble can be rotatable relative to the body to adjust a position of the body relative to the prosthetic stem.

Example 10 is a system for positioning a prosthetic head component with a prosthetic stem. The system can include a stem adapter, a body and a thimble. The stem adapter can have a body configured to engage the prosthetic head component and a neck configured to engage the prosthetic stem, wherein the stem adaptor can include indicia for use with a plurality of indicia of the prosthetic head component. The body can have a plurality of indicia configured in an identical manner to those of the plurality of indicia of the prosthetic head component. The thimble can be configured to couple with the body and mountable to the prosthetic stem. The thimble can be rotatable relative to the body to adjust a position of the body relative to the prosthetic stem.

Example 12 is the system of Example 11, optionally the thimble can include an indicia for use with the plurality of indicia of the body, a relative position between the stem adaptor and the prosthetic head component can be determined by replicating with the indicia of the stem adaptor and the plurality of indicia of the prosthetic head component, the relative positions of the thimble and body as determined using the indicia of the thimble and the plurality of indicia of the body.

Example 13 is the system of any one or combination of Examples 11-12, further optionally including a driver configured to rotate the thimble relative to the body.

Example 14 is the system of any one or combination of of Examples 11-13, optionally the plurality of indicia of the body and the prosthetic head component can each be arranged circumferentially about a centerline axis.

Example 15 is the system of any one of Examples 11-14, optionally the plurality of indicia of the body can be on a distal surface of the body and the body can be translucent such that the plurality of indicia are visible through the body from a side opposing the distal surface.

Example 16 is a method for positioning a prosthetic head component with a prosthetic stem relative to a bone. The method can optionally include any one or combination of: mounting the prosthetic stem to the bone; inserting a thimble within a body; mounting the thimble on the prosthetic stem; adjusting a relative position between the body and the thimble; marking the bone; recreating the relative position with a stem adaptor and the prosthetic head component; marking the prosthetic head component with the aid of an indicia on the stem adaptor once the recreating the relative position with the stem adaptor and the prosthetic head component is achieved; aligning the marking on the bone with the marking on the prosthetic head component; and attaching the prosthetic head component to the prosthetic stem via the stem adaptor.

Example 17 is the method of Example 16, optionally adjusting the relative position between the body and the thimble comprises rotating the thimble relative to the body.

Example 18 is the method of any one or combination of Examples 16-17, optionally recreating the relative position with a stem adaptor and the prosthetic head component comprises positioning, using an indicia of the stem adaptor and a plurality of indicia of the prosthetic head component, the stem adaptor relative to the prosthetic head component and referencing the relative position of the thimble and the body as indicated by an indicia of the thimble and a plurality of indicia of the body.

Example 19 is the method of any one or combination of Examples 16-17, optionally the body can have a plurality of indicia that replicate a plurality of indicia of the prosthetic head component.

Example 20 is the method of any one or combination of Examples 18-19, optionally adjusting a relative position between the body and the thimble references at least one or more edges of the bone, and further can include viewing the indicia of the thimble and the plurality of indicia of the body through a translucent portion of the body.

Example 21 can include, or can optionally be combined with the subject matter of one or any combination of Examples previously recited.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indiciated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for positioning a prosthetic humeral head component with a prosthetic humeral stem relative to a humerus of a patient, comprising:

a stem adapter having a body configured to engage the prosthetic humeral head component and a neck configured to engage the prosthetic humeral stem, wherein the stem adapter includes indicia for use with a plurality of indicia of the prosthetic humeral head component; and a humeral trial apparatus comprising:

a trial humeral head having a plurality of indicia configured in an identical manner to those of the plurality of indicia of the prosthetic humeral head component; and a thimble configured to couple with the trial humeral head and mountable to the prosthetic humeral stem, wherein the thimble is rotatable relative to the trial humeral head to adjust a position of the trial humeral head relative to the prosthetic humeral stem, wherein the trial humeral head defines a recess that comprises a portion of a joint between the trial humeral head and the thimble, wherein the thimble is receivable by the recess, wherein the plurality of indicia of the trial humeral head are on a distal surface of the trial humeral head and arranged circumferentially about a centerline axis of the trial humeral head, wherein the trial humeral head is translucent such that the plurality of indicia are visible through the trial humeral head from a proximal surface of the trial humeral head, wherein the thimble includes one or more indicia for use with the plurality of indicia of the trial humeral head, and wherein a relative position between the stem adapter and the prosthetic humeral head component is determined by replicating, with the indicia of the stem adapter and the plurality of indicia of the prosthetic humeral head component, the relative positions of the thimble and the trial humeral head as determined using the indicia of the thimble and the plurality of indicia of the trial humeral head.

2. The system of claim 1, further comprising a driver configured to rotate the thimble relative to the trial humeral head.

3. The system of claim 1, wherein the plurality of indicia of the prosthetic humeral head component are arranged circumferentially about a centerline axis of the prosthetic humeral head component.

4. The system of claim 1, wherein the trial humeral head is a hemisphere.

5. The system of claim 1, wherein the recess is formed by one or more fingers, and wherein the one or more fingers are configured to elastically deform to retain the thimble in a snap-fit engagement.

6. The system of claim 5, wherein the thimble has a lip configured to be engaged by the one or more fingers when the thimble is inserted in the recess.

7. The system of claim 1, wherein the trial humeral head includes a second recess opposing the joint between the trial humeral head and the thimble, wherein the second recess communicates with the joint between the trial humeral head and the thimble.

8. The system of claim 7, wherein the thimble includes a head on a proximal end thereof, wherein, when the trial humeral head and the thimble are assembled via the joint, the head of the thimble is accessible through the second recess of the trial humeral head.

9. The system of claim 1, wherein the thimble includes one of a recess or a stem, and wherein a finger forms at least a portion of the recess or stem, and wherein the recess or stem of the thimble is configured to elastically deform to retain the thimble on the prosthetic humeral stem.

10. The system of claim 1, wherein the thimble is rotatable relative to the trial humeral head to adjust a position of the trial humeral head relative to the prosthetic humeral stem.

* * * * *